United States Patent [19]

DeVolk et al.

[11] Patent Number: 4,953,980
[45] Date of Patent: Sep. 4, 1990

[54] PARTICLE IDENTIFYING APPARATUS

[75] Inventors: Burton DeVolk, Albuquerque; Fritz Allen, Corrales; Cathy D. Newman; Robert J. Fraatz, both of Albuquerque, all of N. Mex.

[73] Assignee: Mesa Diagnostics, Inc., Albuquerque, N. Mex.

[21] Appl. No.: 228,741

[22] Filed: Aug. 5, 1988

[51] Int. Cl.$^5$ ...................... G01N 21/21; G01N 21/49
[52] U.S. Cl. .................................... 356/338; 356/367
[58] Field of Search ................ 356/336, 338, 367, 368

[56] References Cited

FOREIGN PATENT DOCUMENTS 190628 8/1986 European Pat. Off. ............ 356/338

OTHER PUBLICATIONS

Thompson et al., "Measurement of Polarized Light Interactions via the Mueller Matrix", *Applied Optics*, vol. 19, No. 8, pp. 1323-1332, 4/80.

*Primary Examiner*—Davis L. Willis
*Assistant Examiner*—Matthew W. Koren
*Attorney, Agent, or Firm*—Spensley Horn Jubas & Lubitz

[57] ABSTRACT

Apparatus for identifying a particulate substance in suspension based on the radiation scattering behavior of the substance, which apparatus includes a source of a collimated beam of substantially monochromatic radiation which is linearly polarized along a first polarization axis, at least two modulators disposed in the path of the polarized beam for effecting polarization modulation of the polarized beam about respective dynamic axes at respective modulation frequencies, a sample of the substance being held in the path of the beam between the modulators so that radiation is scattered by the substance in a scattering plane, a polarizing device disposed in the scattering plane for passing that portion of the scattered radiation which is parallel to a second polarization axis, and a signal processing device for producing an indication of the intensity of the radiation emerging from the polarizing device at frequencies corresponding to selected elements of a Mueller matrix which characterizes the scattering properties of the substance, the Mueller matrix being a 4×4 matrix composed of elements fij, where i and j are the row and column numbers, respectively, of each element. The signal processing device derives indications of the intensity of the received radiation corresponding to element f11 of the Mueller matrix and to selected frequency components of the received radiation, which components have amplitudes corresponding to elements f12, f34 and f44 of the Mueller matrix, and the axes are oriented for causing the radiation to contain the selected frequency components.

10 Claims, 3 Drawing Sheets

PARTICLE IDENTIFYING APPARATUS

BACKGROUND OF THE INVENTION

The present invention relates to the identification and characterization of particulate substances, and particularly substances which can be maintained in a static suspension.

It is known that such substances, for example those constituted by biological particles in static suspension, can be identified by subjecting such a suspension to modulated, collimated, monochromatic radiation, modulating and detecting the resulting scattered radiation, and then determining the intensities of various frequency components of the detected radiation, which components correspond to selected elements of a Mueller matrix.

The Mueller matrix is a 4×4 matrix which describes the polarization sensitive transformation of an incident beam of light into a scattered beam of light by a scattering object such as a particle or a suspension of particles. Much information concerning the internal structure and shape of such particles can be derived about the scattering particles from the simultaneous determination of multiple Mueller matrix elements at specific wavelengths and scattering angles, enough information in many cases to enable discrimination among a wide variety of different particles. This can be of considerable clinical significance in the case of biological particles and considerable industrial significance in the case of other types of particles. Measurement of a sufficient number of polarization related phenomena to extract the ten independent Mueller matrix elements would be a formidable task involving many experimental configurations and difficult measurements. However, it is now known that this task can be simplified by deriving all of the relevant information from the measurement of a single intensity using a single apparatus.

Apparatus of this type for identifying biological particles is disclosed in pending U.S. Pat. application Ser. No. 180,686, filed on Apr. 8, 1988, and entitled BIOLOGICAL PARTICLE IDENTIFICATION APPARATUS, this pending application being a continuation of application Ser. No. 893,074, filed on Aug. 1, 1986.

Nevertheless, it has heretofore been considered necessary to derive such information with respect to at least eight matrix elements. When a substance is to be identified by comparing the values derived for this number of matrix elements with values associated with known substances, a substantial quantity of data must be stored and the data processing required to arrive at an identification is both complex and time consuming.

SUMMARY OF THE INVENTION

It is therefore an object of the present invention to reduce the amount of information which must be stored and derived for a given unknown substance to enable identification and/or characterization to be effected.

Another object of the invention is to simplify the data processing operations required to achieve such identification.

A still further object of the invention is to improve the accuracy of the information derived for a substance to be identified by establishing accurate phase relations between the various reference signals employed in the apparatus.

A primary aspect of the invention derives from applicant's discovery that accurate identification of a particulate substance, whether it be a biological substance or a nonbiological substance, can be achieved on the basis of information relating to only four Mueller matrix elements, provided that the four elements in question are properly selected. Specifically, it has been discovered that, for all substances tested to date, an accurate identification can be achieved by deriving scattered radiation intensity values for the Mueller matrix elements f11, f12, f34 and f44, or elements symmetrical thereto.

Other objects of the invention are achieved by novel reference frequency generating circuits which eliminate undesired phase shifts which would otherwise be introduced in the generation of those frequencies.

While it is presently contemplated that the primary utilization of apparatus according to the present invention would be for the identification of biological particles, the invention can also be applied to the identification of nonbiological particles.

A preferred embodiment of the invention which will be described below employs two linear polarizers and two polarization modulators. However, the principles of the invention can be usefully applied to apparatus having other numbers of polarizers and/or modulators.

DESCRIPTION OF THE PREFERRED EMBODIMENTS

Figure 1:
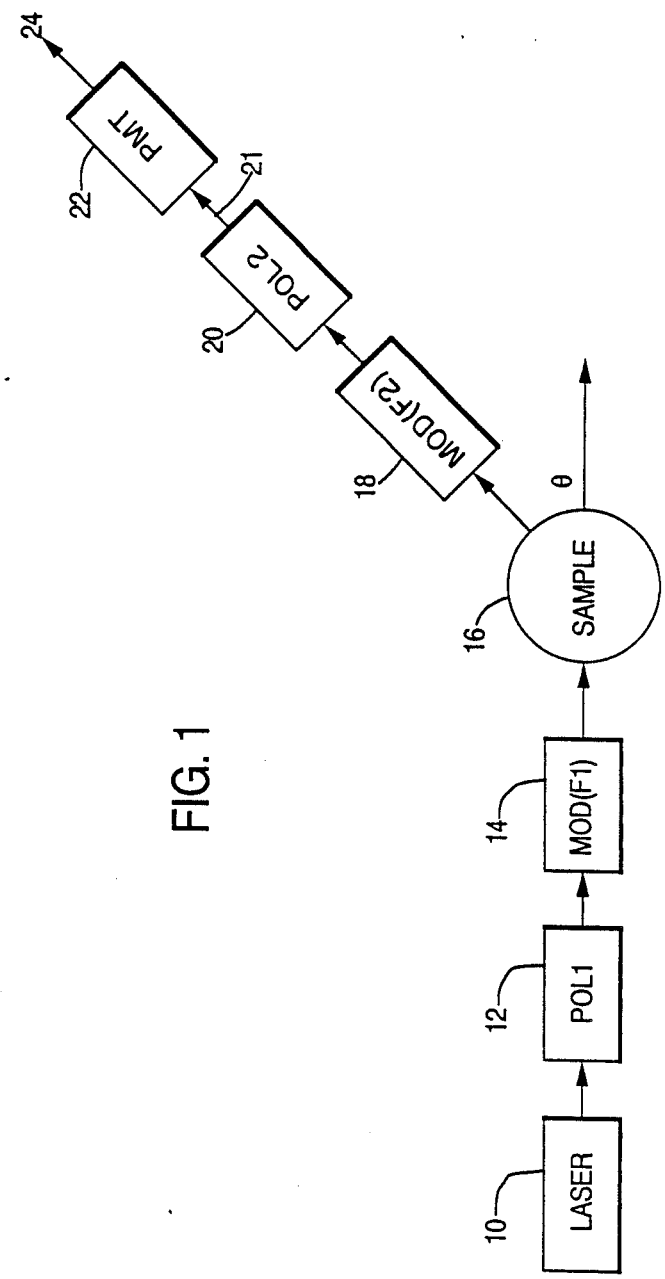
FIG. 1 is a simplified pictorial view of apparatus which can be constructed in accordance with the present invention.

Turning now to the drawings, FIG. 1 is a schematic representation of the basic components of apparatus which can be constructed according to the present invention. Substantially monochromatic light from a light source such as a laser 10 (argon ion laser operating at between 50 and 250 mW output power) is directed into a first polarizer 12 to insure that a substantial fraction of the transmitted radiation is linearly polarized at a specific angle with respect to the horizontal scattering plane. The emerging beam is then directed to a photoelastic modulator 14 operating at 50 kHz wherein the radiation is elliptically polarized with its handedness alternating left and right at 50 kHz. The radiation emerging from the polarization modulator is then made incident on the sample 16 held in a cylindrical quartz cuvette 50 mm in diameter with 2 mm thick walls. The incident intensity is not modulated by these optical elements. Transmitted radiation is directed into a Rayleigh horn (not shown) to minimize stray scattered light.

The scattered light analyzing and detecting components of the present apparatus are mounted on a computer-controlled rotary stage. The scattering angle, θ, in the horizontal plane is defined relative to the incident radiation, and the acceptance half-angle for the analyzing and detecting components was about 0.5°. Scattered radiation to be observed at a particular scattering angle is passed through a second photoelastic modulator 18 which was operated at 53 kHz, and then directed into a second linear polarizer 20. The emerging light 21 is passed through a wavelength filter (not shown) to remove satellite laser wavelengths and fluorescence and is made to impinge on a detector, for example a photomultiplier tube, 22 sensitive to the laser wavelength employed. The retardances of the two modulators 14, 18 were selected to be 2.4048 radians in order to render the total scattered intensity, which is used to normalize the other Mueller matrix elements, independent of the polarization of the scattered light. With the use of two modulators, eight of the Mueller matrix elements can be measured simultaneously; this number being all of the independent matrix elements measurable by any scattering experiments since the remaining matrix elements are derivable therefrom. However, as mentioned above, the present invention requires measurement of only the d.c. matrix element and three additional matrix elements. The two modulation frequencies produce intensity modulation at photomultiplier tube 22 at several frequencies which are linear combinations of the two input frequencies.

One significant aspect of the present invention results from applicant's discovery that reliable identification and/or characterization of virtually any particulate substance capable of being maintained in suspension can be produced on the basis of reference values associated with only four Mueller matrix elements, if those elements are properly selected. Specifically, if in a 4×4 Mueller matrix, each element is identified as fij, where i is the matrix row number and j the matrix column number, the matrix elements which can produce the above result are f11, f12 or f21, f34 or −f43, and f44; f12 and f21 being symmetrical to one another in the Mueller matrix, as are f34 and −f43, for a rotationally averaged scattering suspension.

More specifically, it has been found that comparison of stored values for these four elements with corresponding measured values derived from a sample being tested enables the tested substance to be accurately identified without recourse to comparisons relating to other matrix elements.

It has further been determined that the scattered radiation received by the detector will contain components of one set of the four selected matrix elements only if a specific geometric relation exists between the characteristic axes of the optical components interposed between the collimated monochromatic light source and the detector. Specifically, if the scattering plane, which is the plane of pivotal movement of the arm carrying modulator 18, polarizer 20 and detector 22, represents the reference, or 0°, axis orientation, and all angular values are taken about the radiation axis and in the counterclockwise direction when looking into the radiation beam, i.e., toward the radiation source, the polarization axis of polarizer 1 can have a value of either 45° or 90°. However, if the radiation produced by source 10 has a component in the reference plane, the polarization axis of polarizer 1 can alternatively be oriented at 0°. Then, the characteristic axis of each successive optical component must be oriented at ±45° to that of the preceding component. Specifically, the dynamic axis of the first modulator 14 will be oriented at ±45° to the polarization axis of polarizer 12, the dynamic axis of the second modulator 18 will be oriented at ±45° to the dynamic axis of the first modulator 14, and the polarization axis of the second polarizer 20 will be oriented at ±45° to the dynamic axis of the second modulator 18.

When these relationships are established, and the axis of polarizer 12 is oriented at 0° or 90° to the reference plane, the radiation reaching detector 22 will contain frequency components associated with matrix elements f12, f34 and f44, whereas if the axis of polarizer 12 extends at an angle of 45° to the reference plane, the radiation reaching detector 22 will contain frequency components associated with matrix elements f21, f43 and f44. In any case, the radiation reaching detector 22 will contain a d.c. component associated with matrix element f11.

Two exemplary configurations, or geometries, for the characteristic axes of the four successive optical components are: (1) 90° −45° −90° −45°; and (2) 45° −90° −90°.

The scattered light intensity values associated with these matrix elements correspond, for geometry (1), to the following frequency components of the scattered radiation reaching the detector:

f11 - d.c. component
f12 - $2w_a$
f34 - $w_a \pm 2w_b$
f44 - $w_a \pm w_b$, and for geometry (2):

f11 - d.c. component
f21 - $2w_b$
f43 - $2w_a \pm w_b$
f44 - $w_a \pm w_b$, where $w_a$ is the modulating frequency of modulator 14 and $w_b$ is the modulating frequency of modulator 18.

The specific geometry selected will depend, at least to a certain extent, on the nature of the radiation emitted by source 10. In particular, if that radiation is polarized, the orientation of the polarization axis of the first polarizer 12 must be selected accordingly.

A sample containing an unknown particulate substance in suspension is identified by measuring the received radiation intensity associated with each selected matrix element at each of a series of defined scattering angles Θ, and storing all measured values. The set of measured values forms a pattern characterizing the unknown substance. This pattern can then be compared with stored patterns representing known substances and identification is achieved when the pattern associated with the unknown substance matches a stored pattern within predetermined tolerances.

A specific procedure for deriving information relating to known substances and unknown test substances will now be described. The various angle ranges identified below have been found to provide good results, although for certain types of substances other angular ranges and increments might prove preferable.

The scattered radiation can be measured over a range of scattering angles Θ, which is illustrated in FIG. 1, of between 32° and 120°, and measurements can be made at angular increments, δΘ, of 4°, resulting in measurements at 23 different angles. (Θ=0 extends along the emission axis of the radiation from source 10)

Matrix element values for f11 and f34 are obtained over the entire measuring range, while values for f12 are preferably obtained over the range of 32° to 60° and for f44 over the range of 68° to 120° since these ranges have the greatest information content. The value of δΘ can be varied as desired, smaller values producing higher resolution and larger values leading to shorter measurement times.

A value is derived for each matrix element at each selected angle so that, for a given substance, measurements at 23 different angular setting relating to 4 matrix elements produces 92 separate tests for the substance. In practice, all tests are not used, but a masking function is employed to select the specific ranges mentioned above.

For establishing data relating to each known substance that is to be employed for identifying an unknown substance, a number of test sets are performed for each known substance. All of the values for each test (representing a given value for Θ and a given matrix element) are processed to derive an average value and a standard deviation value. All of the resulting average values and standard deviation values are then stored to constitute the pattern for a given known substance.

When an unknown substance is measured, a complete set of values relating to all associated tests is stored and a rapid pattern recognition method is used to select the known substances which are most likely to correspond to the unknown substance. The patterns relating to the selected known substances are further processed, using the stored standard deviation values, to determine the probability of correspondence of the unknown substance to each of the selected known substances. A multiplicative cumulation is obtained of the area which a selected value range centered on the unknown test value subtends under consideration of the distribution function of experimental results for each test for a given substance. These products can then be compared to determine which of the selected known substances provides the best fit to the unknown substance. It should be noted, however, that in many cases the data derived from the unknown substance can be used directly to provide identification and/or characterization information.

Figure 2:
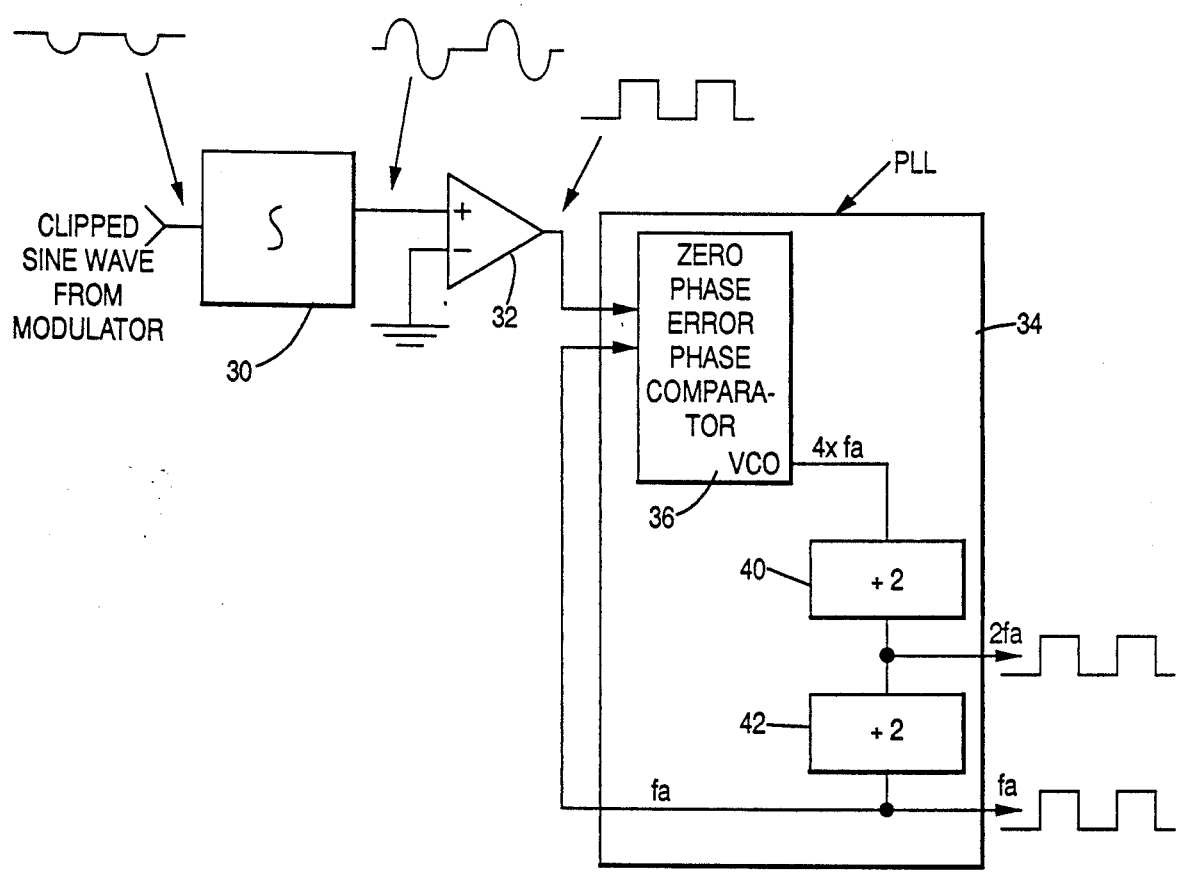
FIGS. 2, 3 and 4 are block circuit diagrams of circuits employed in the generation of reference frequency signals for use in apparatus according to the present invention.

In order to derive the scattered radiation intensity values associated with the selected matrix elements, the output of detector 22 is supplied, possibly through the intermediary of a stabilizing circuit for normalizing all matrix element values as shown in FIG. 2 of application Ser. No. 180,686, cited earlier herein, to a circuit for deriving the d.c. component, associated with matrix element f11, and to three synchronous detectors each set to detect a respective one of the frequencies associated with matrix elements, for example, f12, f34 and f44. By way of a representative example, these frequencies would be, respectively, $2w_a$, $w_a + 2w_b$ and $w_a + w_b$. For this purpose, each synchronous detector, which may be constituted by an element known as a lock-in amplifier described in the above-cited application Ser. No. 180,686, must receive a reference signal at the defined frequency and having a given phase relative to the phase of the associated frequency component in the received radiation.

These reference signals can be derived from the modulating signals applied to modulators 14 and 18, which will be identified herein as signals $V_{ra}$ and $V_{rb}$, which are sinusoidal signals at frequencies $f_a$ and $f_b$, respectively. FIG. 2 illustrates a suitable circuit for deriving from one of those signals square waves at frequencies $f_a$ and $2f_a$, by way of example. The sinusoidal reference signal $V_{ra}$ is converted into a clipped sine wave which is supplied to an integrator 30 having a time constant selected to produce, at its output, a clipped co-sine wave at the same frequency. The latter is applied to a differential amplifier 32 operating as a zero crossing detector to produce a square wave which is synchronized with $f_a$. This square wave signal is supplied to a phase lock loop 34 including a phase comparator 36 of a type selected to produce a zero phase error. Such comparators are known in the art.

The signal at the output of zero crossing detector 32 is applied to one input of comparator 36. Comparator 36 includes a voltage controlled oscillator which outputs a signal at a frequency equal to $4f_a$ and this signal is processed to place it in the form of a square wave which is then subjected to two successive frequency divisions in dividers 40 and 42. The output from divider 42 is fed back to comparator 36 to maintain the desired phase synchronization.

Figure 3:
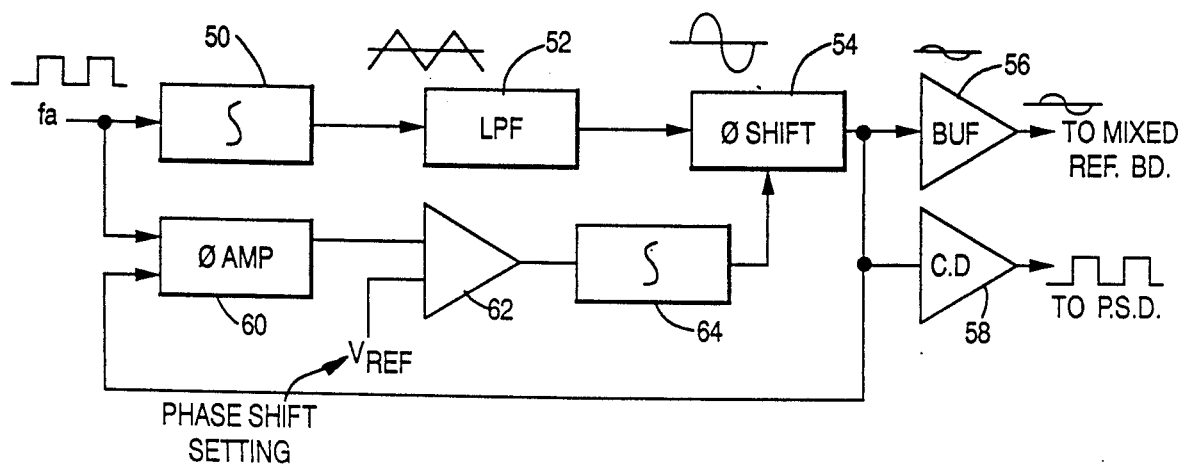

Each output signal from device 34 can then be supplied to a respective circuit of the type illustrated in FIG. 3, which processes the signal at frequency $f_a$, by way of example. This signal is supplied to an integrator 50 having a time constant selected to convert the square wave signal into a signal having a triangular wave form. That signal is supplied to a low pass filter 52 having a time constant selected to produce a sinusoidal signal at frequency $f_a$. The sinusoidal signal is applied to the input of an electrically controllable phase shifter 54 whose output is supplied to a buffer amplifier 56 which provides a smoothed sinusoidal wave at frequency $f_a$ and to a zero-crossing detector 58 which provides a square wave signal at the same frequency. The square wave signal can be employed as the reference signal for a synchronous detector which is to operate at that frequency.

The circuit shown in FIG. 3 further includes a circuit path which acts to control phase shifter 54 in order to eliminate, from the output signal, undesired phase shifts which may be introduced by integrator 50 and/or filter 52. This circuit path includes a phase comparator 60 connected to receive the input signal to integrator 50 and the output signal from phase shifter 54. The output of phase comparator 60, which is a signal proportional to the difference in phase between the two input signals, is applied to a differential amplifier 62 having its second input connected to receive a signal $V_{REF}$ selected to impart the desired phase shift, relative to the signal supplied to integrator 50° to the output signal from shifter 54. The output from amplifier 62 is supplied to an integrator 64 whose output is employed to control the phase shift introduced into the signal by phase shifter 54.

The effect of the circuit path just described is to control the phase shift produced by phase shifter 54 in such a manner as to bring the output signal from differential amplifier 62 to a value of zero. The manner in which this is achieved will be described in greater detail below with reference to FIG. 4.

As explained earlier herein, extraction of the matrix element values contemplated by the present invention requires synchronous detector reference frequencies of $2w_a$ or $2w_b$, $w_a \pm 2w_b$ or $2w_a \pm w_b$, and $w_a \pm w_b$. The first of these reference signals can be derived from the output of detector 58 of a circuit of the type shown in FIG. 3, when a square wave at the frequency $2f_a$ or $2f_b$ ($w = 2\pi f$) is applied to its input.

Figure 4:
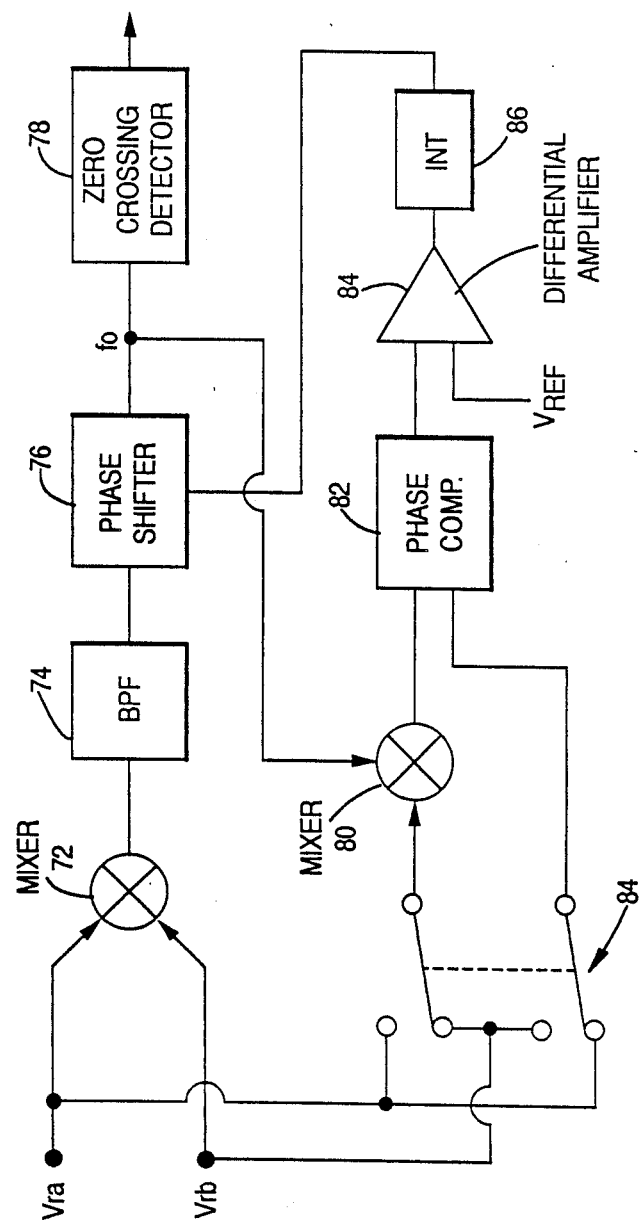

The other reference signals can be derived in the circuit shown in FIG. 4. In that circuit, the inputs signals $V_{ra}$ and $V_{rb}$ will be derived from the buffer amplifiers 56 of respective circuits having the form illustrated in FIG. 3. One generator of the type shown in FIG. 4 will be provided for each desired mixed frequency so that for the first mixed frequency generator, $V_{ra}$ and $V_{rb}$ will be at the frequencies $w_a$ and $2w_b$, or $2w_a$ and $w_b$, while for the other mixed frequency generator, those frequencies will be $w_a$ and $w_b$.

The frequency mixing reference signal generator circuit shown in FIG. 4 has two inputs connected to receive the two input reference signals $V_{ra}$ and $V_{rb}$, which are sinusoidal signals assumed to be, for purposes of the following description, at frequencies $f_a$ and $f_b$. Since signal amplitudes are of no significance to the operation of the circuit, it will be assumed that $V_{ra}$ and $V_{rb}$ each have a peak amplitude of unity and that all circuit units produce outputs having a peak amplitude of unity. $V_{ra} = \cos(w_a t + \phi_1)$ and $V_{rb} = \cos(w_b t + \phi_2)$, where $w_b > w_a$ and $\phi_1$ and $\phi_2$ are the reference signal phases relative to an arbitrarily selected zero phase position.

Signals $V_{ra}$ and $V_{rb}$ are supplied to inputs of a first mixer 72 producing a mixed signal which is supplied to a bandpass filter 74 having a pass-band centered on the frequency $f_o$ of the signal to be produced by the generator. It is assumed here that the center frequency of filter 74 is $f_o = f_a + f_b$. The output signal from filter 74 is:
 $\cos((w_a + w_b)t + \phi_1 + \phi_2 + \phi_3 + \phi_4)$, where $\phi_3$ is the phase shift introduced by mixer 72 and $\phi_4$ is the phase shift introduced by filter 74. This output signal is supplied to a signal controlled phase shifter 76 which introduces a phase shift $\phi_5$ into the signal.

The resulting signal at frequency $f_o$ is then applied to a zero crossing detector 78 producing a square wave output.

While the components described thus far produce an output signal of suitably constant frequency, its phase is subject to fluctuation originating from fluctuations in the operating characteristics of mixer 72 and/or filter 74. Such fluctuations are suppressed by the additional components shown in FIG. 4 in a manner similar to that briefly described above with reference to FIG. 3. These include a second mixer 80 and a phase comparator 82 each having a first input connected to a respective circuit input via a two-position connection interchange switch 84. If $f_o = f_a + f_b$, switch 84 is in the position shown. If $f_o = f_b - f_a$, the position of switch 84 is reversed and filter 74 would be arranged, by adjustment or replacement, to have this new value of $f_o$ as its center frequency.

The second input of mixer 80 is connected to the output of phase shifter 76. Mixer 80 may be followed, if necessary, by one or more suitable notch filters, to suppress undesired harmonics. Thus, the inputs of mixer 80 are:
 $\cos(w_b t + \phi_2)$; and $\cos((w_a + w_b)t + \phi_1 + \phi_2 + \phi_3 + \phi_4 + \phi_5 + \phi_6)$, where $\phi_6$ is a phase shift introduced by mixer 80° and the output is:
 $\cos(w_a t + \phi_1 + \phi_3 + \phi_4 + \phi_5 + \phi_6)$.
This output is supplied to the second input of phase comparator 82. Phase comparator 82 is preferably of a known type which will produce an output responsive only to input signals at the same frequency. Therefore, with respect to the signal at the second input of comparator 82, only the component at frequency $w_a$ will influence the comparator output. Since the first input of comparator 82 receives $\cos(w_a t + \phi_1)$, the comparator output voltage, $V_c$, is:
 $F(\phi_3 + \phi_4 + \phi_5 + \phi_6)$, where F is a monotonic function which in most cases can be linear.

Phases $\phi_3$, $\phi_4$ and $\phi_5$ are introduced in the forward signal generating path of the circuit and contribute directly to the phase of the output signal. Phase $\phi_6$ is the residual phase created by mixer 82 and can be kept to a negligible level by giving mixer 82 a signal bandwidth $> 100 f_b$, so that $\phi_6$ can be treated as a constant of very small magnitude. Thus, the output signal from phase comparator 82 will vary with changes in $\phi_3$, $\phi_4$ and $\phi_5$.

The output of phase comparator 82 is supplied to one input of a differential amplifier 84 whose other input receives an adjustable reference voltage $V_{ref}$. The output of amplifier 84 is applied to the input of an integrator 86 and the output of integrator 86 is connected to control the phase shift produced by phase shifter 76.

Phase shifter 76 is constructed to respond to the output signal from integrator 86 to vary $\phi_5$ in the direction to oppose any change in $\phi_3$ or $\phi_4$ so that the control action effected on phase shifter 76 will tend to bring the output of amplifier 84 to zero, corresponding to $F(\phi_3 + \phi_4 + \phi_5 + \phi_6) = V_{ref}$. Once this state has been established, it will be maintained by the output signal from integrator 86 until some change occurs in $\phi_3$ or $\phi_4$. Thus, any change occurring in $\phi_3$ or $\phi_4$ will be neutralized so that the output signal phase will vary only in response to changes in $\phi_1$ and $\phi_2$.

If the frequency-difference output is to be produced, the control will be effected according to the same principle.

Thus, the circuits shown in FIGS. 2–4 provide synchronous detector reference signals bearing accurately defined phase relations to the modulation signals supplied to modulators 14 and 18. This assures that the intensity of the frequency components of interest in the received radiation will be measured with a high degree of accuracy and reliability, which, in turn, will lead to a more accurate substance identification and/or characterization.

While the description above shows particular embodiments of the present invention, it will be understood that many modifications may be made without departing from the spirit thereof. The pending claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In apparatus for identifying a particulate substance in suspension based on the radiation scattering behavior of the substance, which apparatus includes means for generating a collimated beam of substantially monochromatic radiation which is linearly polarized along a first polarization axis transverse to the beam axis, first modulation means disposed in the path of the linearly polarized beam for effecting polarization modulation of the linearly polarized beam about a first dynamic axis at a first modulation frequency; means for holding a sample of the particulate substance in the path of the modulated beam emerging from said first modulation means so that radiation is scattered by the substance in a scattering plane, second modulation means disposed in the scattering plane for receiving radiation scattered by the sample and effecting polarization modulation of the scattered radiation about a second dynamic axis at a second modulation frequency; polarizing means disposed in the scattering plane for receiving scattered radiation from said second modulation means and having a second polarization axis for passing that portion of the scattered radiation which is parallel to the second polarization axis; detector means connected to receive radiation passed by said polarizing means and to produce a signal corresponding to the intensity of that radiation; and signal processing means connected to receive the signal for producing an indication of the intensity of the radiation received by the detector means at frequencies corresponding to selected elements of a Mueller matrix which characterizes the radiation scattering properties of the substance, the Mueller matrix being a 4×4 matrix composed of element fiji, where i is the row number and j is the column number of each element, the improvement wherein aid signal processing means are operative for only deriving indications: of the intensity of the received radiation corresponding to element f11 of the Mueller matrix; and of three selected frequency components of the received radiation, which components have amplitudes corresponding to elements f12, f34 and f44 of the Mueller matrix, and said polarization axes and dynamic axes are oriented for causing the radiation arriving at said detector means to contain said selected frequency components.

2. Apparatus as defined in claim 1 wherein said selected frequency components are associated with elements f21, −f43 and f44 of the Mueller matrix.

3. Apparatus as defined in claim 1 wherein said first polarization axis extends at an angle of 0°, plane which differs by ±45° from that of said first dynamic axis extends at an angle to aid scattering plane which differs by ±45° from that of said first polarization axis, said second dynamic axis extends at an angle to said scattering plane which differs by ±45° from that of said first dynamic axis, and said second polarization axis extends at an angle to said scattering plane which differs by ±45° from that of said second dynamic axis.

4. Apparatus as defined in claim 1 wherein said means for generating a collimated beam comprise second polarizing means defining said first polarization axis.

5. In apparatus for identifying a particulate substance in suspension based on the radiation scattering behavior of the substance, which apparatus includes means for generating a collimated beam of substantially monochromatic radiation which is linearly polarized along a first polarization axis transverse to the beam axis, first modulation means disposed in the path of the linearly polarized beam for effecting polarization modulation of the linearly polarized beam about a first dynamic axis at a first modulation frequency; means for holding a sample of the particulate substance in the path of the modulated beam emerging from said first modulation means so that radiation is scattered by the substance in a scattering plane, second modulation means disposed in the scattering plane for receiving radiation scattered by the sample and effecting polarization modulation of the scattered radiation about a second dynamic axis at a second modulation frequency; polarizing means disposed in the scattering plane for receiving scattered radiation from said second modulation means and having a second polarization axis for passing that portion of the scattered radiation which is parallel to the second polarization axis; detector means connected to receive radiation passed by said polarizing means and to produce a signal corresponding to the intensity of that radiation, and signal processing means connected to receive the signal for producing an indication of the intensity of the radiation received by the detector means at frequencies corresponding to selected elements of a Mueller matrix which characterizes the radiation scattering properties of the substance, the Mueller matrix being a 4 ×4 matrix composed of elements fig, where i is the row number and j is the column number of each element, the improvement wherein said signal processing means comprise means for deriving an indication of the intensity of the received radiation corresponding to element f11 of the Mueller matrix and indications of selected frequency components of the received radiation, which components have amplitudes corresponding to elements f12, f34 and f44 of the Mueller matrix, and said polarization axes and dynamic axes are oriented for causing the radiation arriving at said detector means to contain said selected frequency components, and wherein aid means for deriving comprise synchronous detection means connected to receive a reference frequency signal at one of said selected frequency components for detecting the intensity of the received radiation at that frequency, and circuit means for generating the reference frequency signal, said circuit means comprising: signal modifying means connected to derive from at least one input signal an output signal having a frequency which is a function of the frequency of the at least one input signal and a phase which is a function of the phase of the at least one input signal and having a phase shift produced by said signal modifying means; controllable phase shift means connected to introduce an additional phase shift into the output signal; and phase shift control means responsive to the phase of the output signal and connected to said phase shift means for controlling said phase shift means in a manner to maintain the sum of the phase shift produced by said signal modifying means and the additional phase shift at a constant value.

6. In a method for identifying a particulate substance in suspension based on the radiation scattering behavior of the substance, which method includes: producing a collimated beam of substantially monochromatic radiation which is linearly polarized along a first polarization axis transverse to the beam axis, effecting a first polarization modulation of the linearly polarized beam about a first dynamic axis at a first modulation frequency; directing the beam, subsequent to the first polarization modulation, into a sample of the particulate substance so that radiation is scattered by the substance in a scattering plane; effecting a second polarization modulation of scattered radiation in the scattering plane about a second dynamic axis at a second modulation frequency; effecting a linear polarization, along a second polarization axis, of scattered radiation which has been subjected to the second polarization modulation for passing that portion of the scattered radiation which is parallel to the second polarization axis; detecting the scattered radiation which has been subjected to the linear polarization to produce a signal corresponding to the intensity of that radiation; and processing the signal for producing an indication of the intensity of the detected radiation at frequencies corresponding to selected elements of a Mueller matrix which characterizes the radiation scattering properties of the substance, the Mueller matrix being a 4 ×4 matrix composed of elements fig, where i is the row number and j is the column number of each element, the improvement wherein said step of processing comprise deriving an indication only; of the intensity of the received radiation corresponding to element f11 of the Mueller matrix; and of three selected frequency components of the received radiation, which components have amplitudes corresponding to elements f12, f34 and f44 of the Mueller matrix, and said method further comprises orienting the first and second polarization axes and the first and second dynamic axes for causing the detected radiation to contain said selected frequency components.

7. A method as defined in claim 6 wherein said selected frequency components are associated with elements f21, −f43 and f44 of the Mueller matrix.

8. A method as defined in claim 6 wherein said first polarization axis extends at an angle of 0°, ±45° or ±90° to said scattering plane, said first dynamic axis extends at an angle to said scattering plane which differs by ±45° from that of said first polarization axis, said second dynamic axis extends at an angle to said scattering plane which differs by ±45° from that of said first dynamic axis, and said second polarization axis extends at an angle to said scattering plane which differs by ±45° from that of said second dynamic axis.

9. A method as defined in claim 6 wherein said step of producing a collimated beam includes effecting a first linear polarization of the beam by a polarizing device defining said first polarization axis and located in the path of the collimated beam.

10. In a method for identifying a particulate substance in suspension based on the radiation scattering behavior of the substance, which method includes directing a collimated beam of substantially monochromatic radiation from a source of such radiation into a sample of the substance so that the radiation is scattered by the substance in a scattering plane, detecting radiation which has been scattered in the scattering plane to produce a signal corresponding to the intensity of that radiation, effecting linear polarization and polarization modulation of the radiation between the source and the detector, and processing the signal for producing an indication of the intensity of the detected radiation at frequencies corresponding to selected elements of a Mueller matrix which characterizes the radiation scattering properties of the substance, the Mueller matrix being a 4 ×4 matrix composed of elements fig, where i is the row number and j is the column number of each element, the improvement wherein said step of processing comprises deriving only: an indication of the intensity of the received radiation corresponding to element f11 of the Mueller matrix; and indications of three selected frequency components of the received radiation, which components have amplitudes corresponding to elements f12, f34 and f44 of the Mueller matrix, and said step of effecting linear polarization and polarization modulation of the radiation is carried out in a manner to cause the detected radiation to contain said selected frequency components.

* * * * *